(12) United States Patent
Buyda et al.

(10) Patent No.: US 11,051,849 B2
(45) Date of Patent: Jul. 6, 2021

(54) CANNULA ASSEMBLY WITH COLLAPSIBLE FIXATION DEVICE

(71) Applicant: Covidien LP, Mansfield, MA (US)

(72) Inventors: Oksana Buyda, East Haven, CT (US); Amanda Adinolfi, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 124 days.

(21) Appl. No.: 16/279,169

(22) Filed: Feb. 19, 2019

(65) Prior Publication Data

US 2019/0307486 A1 Oct. 10, 2019

Related U.S. Application Data

(60) Provisional application No. 62/653,859, filed on Apr. 6, 2018.

(51) Int. Cl.
*A61B 17/34* (2006.01)
*A61B 17/00* (2006.01)

(52) U.S. Cl.
CPC ...... *A61B 17/3423* (2013.01); *A61B 17/3421* (2013.01); *A61B 17/3462* (2013.01); *A61B 17/3498* (2013.01); *A61B 17/3474* (2013.01); *A61B 2017/0042* (2013.01); *A61B 2017/00907* (2013.01); *A61B 2017/00951* (2013.01); *A61B 2017/3484* (2013.01); *A61B 2017/3488* (2013.01); *A61B 2017/3492* (2013.01)

(58) Field of Classification Search
CPC ............ A61B 17/3421; A61B 17/3423; A61B 17/3462; A61B 17/3498; A61B 17/3474; A61B 17/3496; A61B 17/3417; A61B 17/3431; A61B 17/34; A61B 2017/0042; A61B 2017/00951; A61B 2017/348; A61B 2017/3484; A61B 2017/3488; A61B 2017/3492; A61B 2017/3465; A61B 2017/3419; A61B 2017/00986; A61F 2/0063; A61F 2002/0072
USPC ......................................................... 604/174
See application file for complete search history.

(56) References Cited

U.S. PATENT DOCUMENTS 5,122,122 A * 6/1992 Allgood ................. A61B 17/34
604/105
5,716,329 A * 2/1998 Dieter .................... A61B 1/303
600/184
5,836,913 A 11/1998 Orth et al.
(Continued)

OTHER PUBLICATIONS

European Search Report dated Aug. 6, 2019, issued in EP Appln. No. 19167567.

*Primary Examiner* — Ashley L Fishback
*Assistant Examiner* — Uyen N Vo

(57) ABSTRACT

A cannula assembly includes a housing supporting a seal assembly, a cannula shaft extending from the housing, and a sleeve positioned about the cannula shaft including an inner fixation device that is supported on a distal end of the cannula shaft. The inner fixation device includes an anchor member that is deployable within a body cavity to obstruct withdrawal of the cannula assembly from within the body cavity. The anchor member is formed of a material that will deactivate or allow removal of the catheter assembly from the body cavity when the anchor member is deployed and an excessive force is applied to the cannula assembly to prevent ripping or tearing of tissue.

15 Claims, 6 Drawing Sheets

(56) References Cited

U.S. PATENT DOCUMENTS

| | | | |
|---|---|---|---|
| 8,002,750 B2* | 8/2011 | Smith | A61B 17/3462 604/167.03 |
| 8,740,925 B2 | 6/2014 | Bettuchi et al. | |
| 2002/0193806 A1* | 12/2002 | Moenning | A61M 25/02 606/108 |
| 2005/0004592 A1* | 1/2005 | Criscuolo | A61B 17/0218 606/190 |
| 2007/0162066 A1* | 7/2007 | Lyon | A61B 17/3421 606/191 |
| 2010/0152664 A1* | 6/2010 | Davis | A61B 17/3494 604/164.03 |

\* cited by examiner

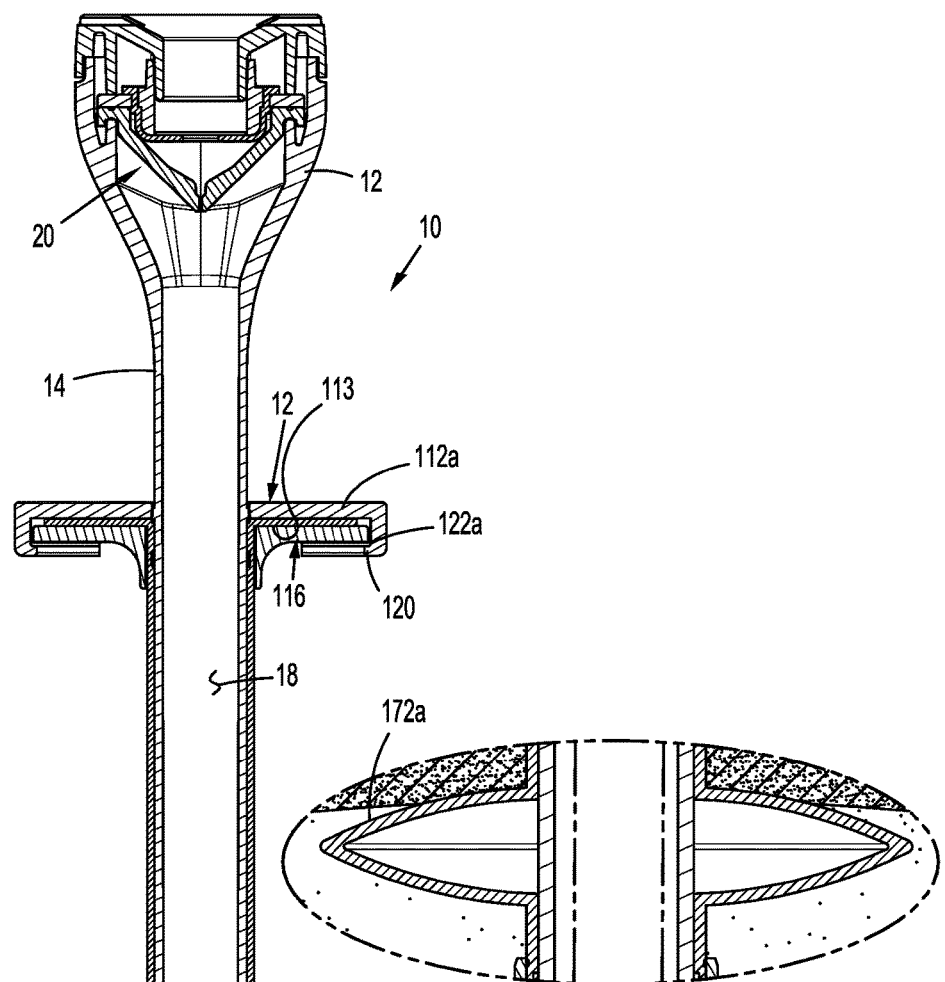
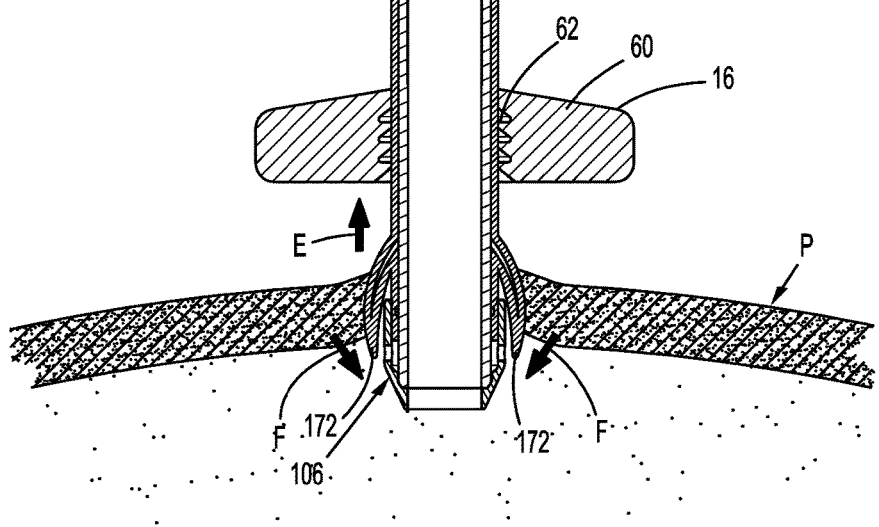
FIG. 4B
FIG. 4A

CANNULA ASSEMBLY WITH COLLAPSIBLE FIXATION DEVICE

CROSS-REFERENCE TO RELATED APPLICATIONS

This application claims the benefit of and priority to U.S. Provisional Patent Application Ser. No. 62/653,859 filed Apr. 6, 2018, the entire disclosure of which is incorporated by reference herein.

BACKGROUND

1. Technical Description

The present disclosure is directed to a cannula assembly and, more particularly, to a cannula assembly including a collapsible fixation device.

2. Background of Related Art

Cannula assemblies are commonly used during endoscopic surgical procedures to provide access to a body cavity for surgical instrumentation while maintaining a seal on the body cavity. The seal on the body cavity prevents loss of insufflation gases through an incision into the body cavity. Typically, a cannula assembly includes an anchor or fixation device that is provided to secure the cannula assembly within the body cavity. When the fixation device is deployed, it obstructs removal of the cannula assembly through the incision from within the body cavity. When a large force is applied to the cannula assembly with the fixation device deployed, either intentionally or unintentionally, the skin is subject to tearing or ripping.

A continuing need exists in the surgical arts for a cannula assembly that minimizes the likelihood that tissue tearing may occur due to external forces applied to the cannula assembly.

SUMMARY

One aspect of the present disclosure is directed to a cannula assembly that includes a housing, a cannula shaft, and a sleeve. The housing defines a receptacle and a seal assembly is positioned within the receptacle. The seal assembly is adapted to form a seal about a surgical instrument inserted through the housing. The cannula shaft extends from the housing and defines a channel. The channel defines a longitudinal axis and has a proximal portion that communicates with the receptacle and an open distal end. A sleeve is supported about the cannula shaft and has a proximal portion movably positioned about the cannula shaft and a distal portion axially fixed to a distal portion of the cannula shaft. The sleeve has a deformable mesh material with a deployable anchor member and a thin elastomeric cover that extends from the proximal portion of the sleeve to a lower portion of the sleeve leaving the anchor member uncovered. A frustoconical end cap is attached to the cannula shaft at the distal end thereof so as to cover the distal portion of the sleeve and has one or more holes for receiving an adhesive material. Movement of the proximal portion of the sleeve towards the distal portion of the sleeve causes the anchor member to move radially outward away from the longitudinal axis of the cannula shaft. The anchor member is formed of a material that is configured to allow movement of the anchor member inwardly towards the cannula shaft when a force is applied to the cannula assembly to facilitate removal of the cannula assembly from within a body cavity of a patient.

In certain embodiments, the cover is formed from a transparent material. The cannula assembly can include a grip assembly secured to the proximal portion of the sleeve. In certain embodiments, the sleeve defines a flange at an upper end thereof, and the flange extends radially outwardly. The grip assembly can include a first portion and a second portion, and the flange can be clamped between the first portion and the second portion of the grip assembly.

In embodiments, the cannula assembly can include an outer fixation member slidably positioned about the cannula shaft. The outer fixation member can be positioned about the sleeve and cannula shaft. The housing can include a fluid port, the fluid port defining a bore that communicates with the receptacle. The cannula assembly can support a valve housing that is positioned to control fluid flow through the bore of the fluid port. The valve can be a rotary valve and/or stopcock.

Another aspect of the disclosure is directed to a cannula assembly including a housing, a seal assembly, a cannula shaft, and a sleeve. The housing defines a receptacle. The seal assembly is positioned within the receptacle and is adapted to form a seal about a surgical instrument inserted through the housing. The cannula shaft extends from the housing and defines a channel defining a longitudinal axis. The cannula shaft has a proximal portion that communicates with the receptacle and an open distal end. The sleeve has a proximal portion movably positioned about the cannula shaft and a distal portion axially fixed to a distal portion of the cannula shaft. The sleeve is formed from a mesh material including mesh filaments, and a protective cover. Movement of the proximal portion of the sleeve towards the distal portion of the sleeve causes the distal portion of the sleeve to move outwardly from the longitudinal axis of the cannula shaft to form an anchor member adjacent the distal portion of the cannula shaft, the protective cover extending from the proximal portion of the sleeve and leaving the anchor member uncovered.

In certain embodiments, the protective cover is formed of a transparent material.

In embodiments, the cannula assembly also includes a grip assembly secured to the proximal portion of the sleeve.

In some embodiments, the sleeve includes a flange that extends radially outwardly from the cannula shaft.

In certain embodiments, the grip assembly includes a first portion and a second portion, wherein the flange is clamped between the first and second portions of the grip assembly.

In embodiments, the cannula assembly also includes an end cap supported on the distal portion of the cannula shaft, and the distal portion of the sleeve is axially fixed in relation to the cannula shaft between an inner surface of the end cap and an outer surface of the cannula shaft.

In some embodiments, a distal portion of the end cap is frusto-conically shaped. The end cap can define one or more holes for the receipt of an adhesive material.

In certain embodiments, the cannula assembly also includes an outer fixation member slidably positioned about the cannula shaft.

BRIEF DESCRIPTION OF THE DRAWINGS

Various embodiments of the presently disclosed cannula assembly are described herein below with reference to the drawings, wherein:

FIG. 4A is a cross-sectional view taken along section line 4-4 of FIG. 1 with the anchor member in a deployed configuration as the anchor member deactivates in response to an excessive force applied to the cannula assembly;

FIG. 4B is an area of detail as shown on FIG. 4;

DETAILED DESCRIPTION OF EMBODIMENTS

Figure 1:
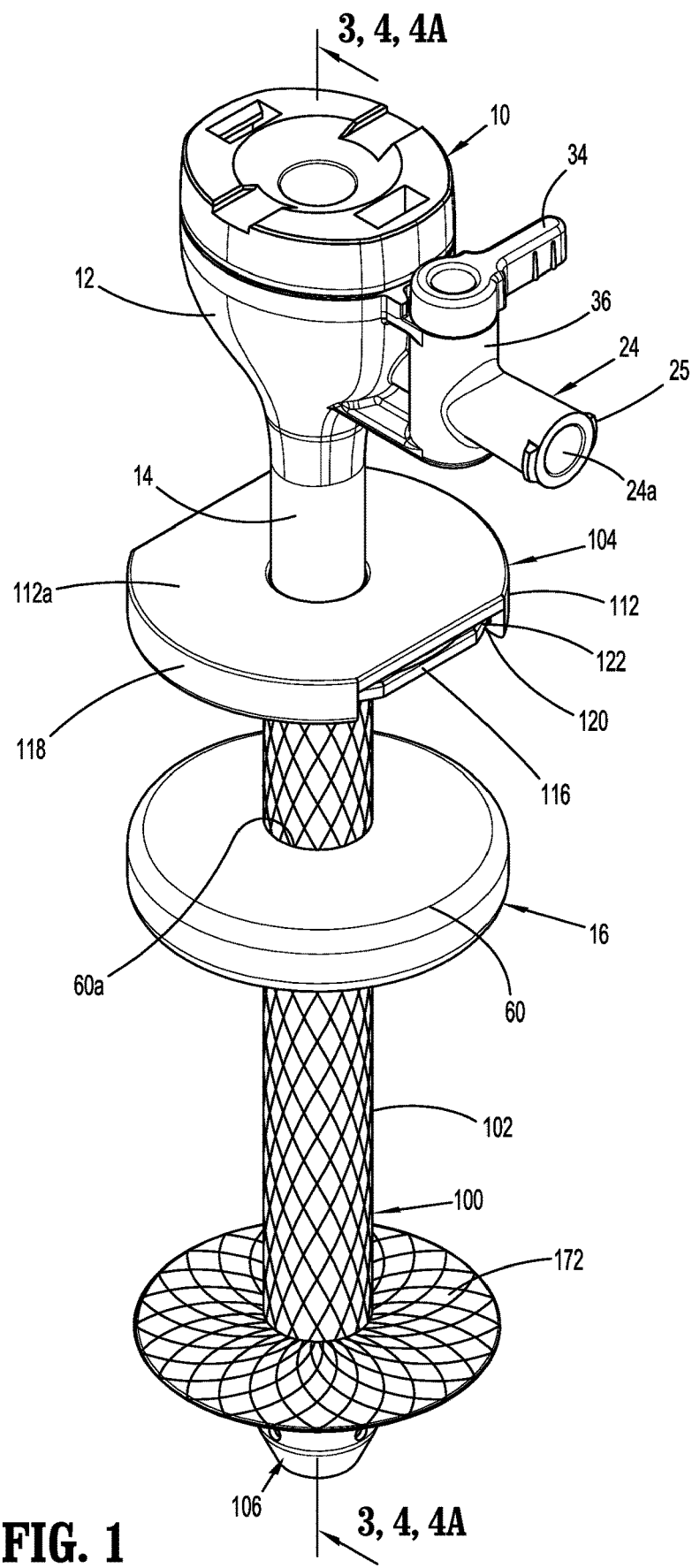
FIG. 1 is a side perspective view of an exemplary embodiment of the presently disclosed cannula assembly with an anchor member in a deployed configuration.

The presently disclosed cannula assembly will now be described in detail with reference to the drawings in which like reference numerals designate identical or corresponding elements in each of the several views. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "endoscopic" is generally used to refer to endoscopic, laparoscopic, arthroscopic, and/or any other procedure conducted through small diameter incision or cannula. Further, the term "clinician" is used generally to refer to medical personnel including doctors, surgeons, nurses, and support personnel, and the term "about" means plus or minus 10 percent of a given parameter.

Figure 2:
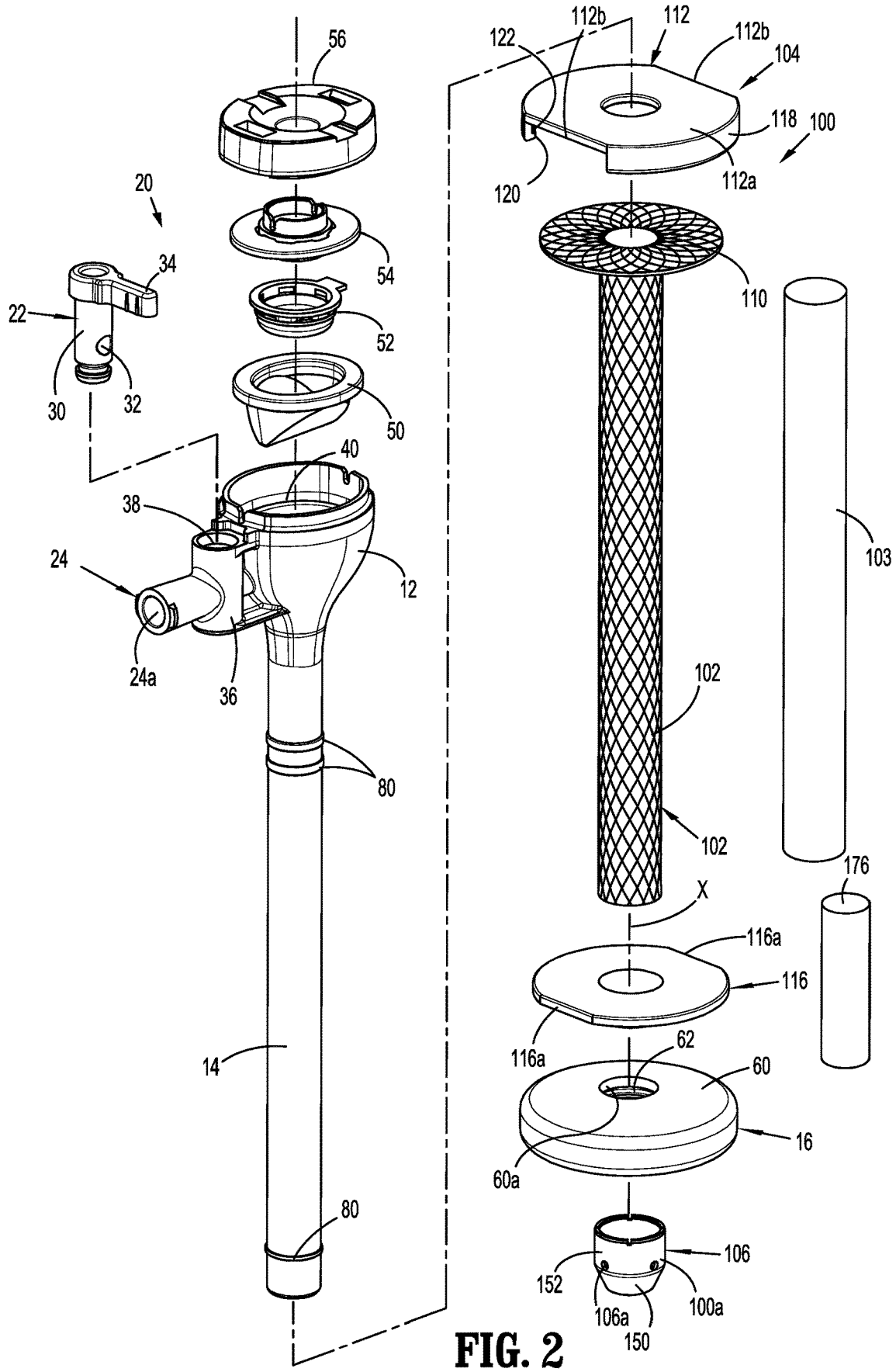
FIG. 2 is an exploded, side, perspective view of the cannula assembly shown in FIG. 1.

Referring to FIGS. 1 and 2, the presently disclosed cannula assembly is shown generally as cannula assembly 10. The cannula assembly 10 includes a housing 12, a cannula shaft 14 extending from the housing 12, an outer fixation device 16, and an inner fixation device 100. The cannula shaft 14 defines a channel 18 (FIG. 3) that extends between the housing 12 and a distal end of the cannula shaft 14. The housing 12 supports a seal assembly 20 (FIG. 2) and a valve 22. The housing 12 also includes a fluid port 24 that defines a bore 24a that communicates with the channel 18 of the cannula shaft 14. The valve 22 is positioned on the housing 12 to allow a clinician to control fluid flow through the fluid port 24. In embodiments, the fluid port 24 includes a luer type connector 25 or the like and can be attached to a source of pressurized gas, e.g., carbon dioxide. The valve 22 can be actuated to direct the pressurized gas into the channel 18 to insufflate a body cavity "BC" (FIG. 3) during an endoscopic surgical procedure.

In embodiments, the valve 22 includes a cylindrical shaft 30 (FIG. 2) that defines a through bore 32 and a valve handle 34. The valve 22 is supported within a valve housing 36 supported on the housing 12 of the cannula assembly 10. The valve housing 36 defines a cylindrical bore 38 (FIG. 2) that communicates with the bore 24a of the fluid port 24. The valve 22 is positioned within the valve housing 36 such that the through bore 32 can be rotated into and out of registration with the bore 24a of the fluid port 24a to control fluid flow from the fluid port 24 into a receptacle 40 of the housing 12. Alternately, the use of other valve types is envisioned.

Figure 3:
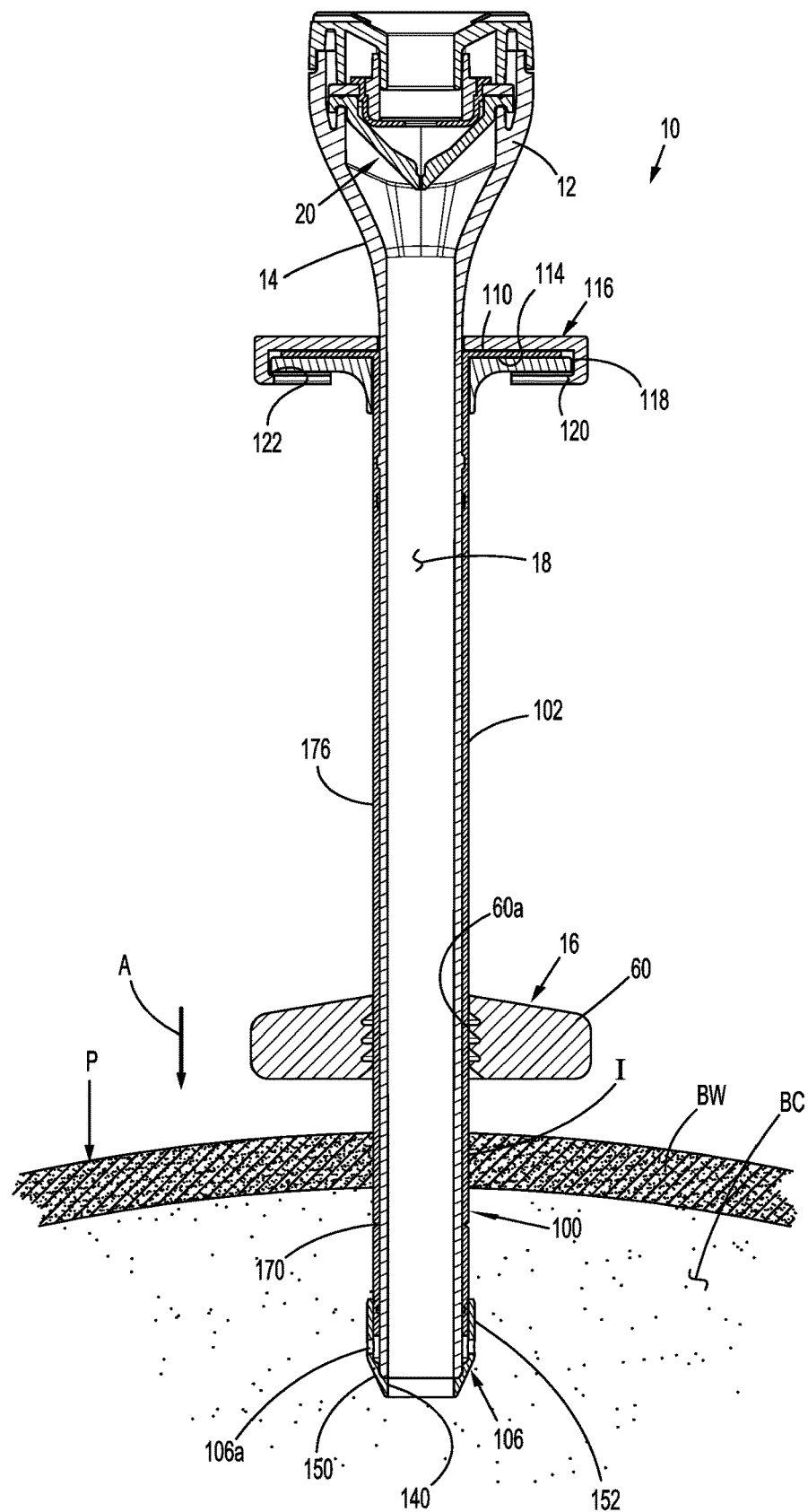
FIG. 3 is a cross-sectional view taken along section line 3-3 of FIG. 1 with the anchor member in a non-deployed configuration.

Referring also to FIG. 3, the seal assembly 20 is supported within the receptacle 40 defined by the housing 12 and includes a zero closure valve 50, an instrument seal 52, a seal mount 54, and a cap 56. The zero closure valve 50 is adapted to open to permit passage of a surgical instrument (not shown) through the housing 12 or close when the surgical instrument is not present within the housing 12. The instrument seal 52 is adapted to provide a fluid tight seat about a surgical instrument that is positioned through the cannula assembly 10 during a surgical procedure. The seal mount 54 and cap 56 are adapted properly position and secure the components of the seal assembly 20 within the receptacle 40 of the housing 12 of the cannula assembly 10. U.S. Pat. No. 8,740,925 (the '925 Patent) discloses a trocar assembly including a seal assembly similar to that described above. The '925 Patent is incorporated herein in its entirety by reference.

The outer fixation device 16 and the inner fixation device 100 are provided to secure the cannula assembly 10 to a patient "P" with the cannula shaft 14 extending through a small incision "I" (FIG. 3) in the patient "P". The outer fixation device 16 can have a variety of different configurations and is provided to be positioned adjacent an external surface of the patient "P" to secure the cannula assembly 10 in place. In embodiments, the outer fixation device 16 includes an annular body 60 that is received about and slidable along the cannula shaft 14. In some embodiments, the inner wall may be configured or dimensioned to grip or frictionally engage the outer surface of the cannula shaft 14. For example, the annular body 60 can be formed of a flexible material and define an opening 60a having an inner diameter that is less than the outer diameter of the cannula shaft 14. In such embodiments, the annular body 60 can be stretched to a position about the cannula shaft 14 such that the axial position of the outer fixation device 16 is retained along the cannula shaft 14 via engagement between the annular body 60 and the cannula shaft 14. As shown, the inner surface of the outer fixation device 16 in contact with the cannula shaft 14 (via the inner fixation device 100) may include teeth 62 (FIG. 3) that are angled to facilitate distal movement of the outer fixation device 16 along the cannula shaft 14 but to obstruct proximal movement of the outer fixation device 16 along the cannula shaft 14. Alternately, other clamping or locking devices can be used to secure the outer portion of the cannula assembly 10 to a patient "P".

The inner fixation device 100 includes an expandable and collapsible sleeve 102, a grip assembly 104, and an end cap 106. The sleeve 102 is positioned about the cannula shaft 14 and extends from a proximal portion of the cannula shaft 14 to a distal portion of the cannula shaft 14. In embodiments, the proximal portion of the sleeve 102 is positioned distally of the housing 12. Alternately, it is envisioned that the sleeve 102 can extend to a position adjacent or proximally of the housing 12.

The grip assembly 104 is secured to a proximal portion of the sleeve 102 and is adapted to move the sleeve 102 axially along the cannula shaft 14 when the grip assembly 104 is moved axially along the cannula shaft 14. In embodiments, the proximal portion of the sleeve 102 includes a flange portion 110 that extends radially outwardly from a longitudinal axis "X" (FIG. 2) defined by the sleeve 102. In addition, the grip assembly 104 includes a first portion 112 and a second portion 116. The first portion 112 defines a recess 114 (FIG. 3) that is dimensioned to receive the flange portion 110 of the sleeve 102. The first portion 112 also includes a proximal wall 112a that defines a plane that is perpendicular to the longitudinal axis "X" of the sleeve 102 and a side wall 118 that extends in a distal direction along the outer periphery of the proximal wall 112a. A distal end of the side wall 118 includes an extension 120 that extends radially inward toward the longitudinal axis "X" of the sleeve 102 a short distance to define a shelf 122 (FIG. 3). In embodiments, the first portion 112 includes at least one truncated portion 112b.

The second portion 116 of the grip assembly 104 has a configuration that is substantially similar to the configuration of the proximal wall 112a of the first portion 112. In embodiments, the second portion 116 also includes at least one truncated portion 116a. In embodiments, each of the first and second portions 112, 116, respectively, include first and second truncated portions 116a that are diametrically offset from each other.

In order to secure the grip assembly 104 to the proximal portion of the sleeve 102, the flange portion 110 of the sleeve 102 is positioned against an inner surface 113 (FIG. 3) of the proximal wall 112a of the first portion 112 of the grip assembly 104 and the second portion 116 of the grip assembly 104 is slid proximally along the sleeve 102 and the cannula shaft 14. When the second portion 116 of the grip assembly 104 is positioned adjacent the first portion 112 of the grip assembly 104, the second portion 116 can be deformed and snap fit past the extension 120 of the first portion 112 and onto the shelf 122 of the extension 120 to clamp the flange portion 110 of the sleeve 102 between an inner surface of the proximal wall 112a of the first portion 112 and a distal face of the second portion 116. Thus, axial movement of the grip assembly 104 along the cannula shaft 14 causes corresponding movement of the proximal portion of the sleeve 102 about the cannula shaft 14. Alternatively, the flange portion 110 of the sleeve 102 can be omitted and the grip assembly 104 can be one or more plastic parts otherwise attached to the sleeve 102 using adhesives, welding, or other methods. The grip assembly first portion 112 and second portion 116 can be molded plastic parts that are attached to the sleeve 102 (to the flange portion 110 or otherwise), or the grip assembly can be overmolded onto the sleeve 102.

In embodiments, the distal portion of the sleeve 102 is secured to the distal portion of the cannula shaft 14 using the end cap 106. The end cap 106 is annular in shape and includes longitudinal bore 140 that is aligned with the channel 18 of the cannula shaft 14 when the end cap 106 is secured to the distal portion of the cannula shaft 14. In embodiments, the distal portion 150 of the end cap 106 has a frusto-conical shape and the proximal portion 152 has a cylindrical shape and is dimensioned to receive the distal portion of the cannula shaft 14. The frusto-conical shape of the distal portion 150 of the end cap 106 facilitates entry of the cannula assembly 10 into an incision in a patient "P". In order to secure the distal portion of the sleeve 102 to the distal portion of the cannula shaft 14, the distal portion of the sleeve 102 is positioned between an inner wall of the proximal portion 152 of the end cap 106 and an outer wall of the cannula shaft 14. The end cap 106 can be press-fit onto the cannula shaft 14 about the sleeve 102 to secure the end cap 106 and the sleeve 102 to the cannula shaft 14. In addition, the end cap 106 can be secured to the cannula shaft 14 using adhesives or ultrasonic welding. The end cap 106 can include holes 106a that facilitate the passage of adhesive through the holes. Alternatively, the end cap 106 can be formed on the sleeve 102 using overmolding techniques, or an end cap can be attached using welding.

Referring to 2-4, the grip assembly 104 can be slid distally about the cannula shaft 14 to advance the sleeve 102 about the cannula shaft 14 towards the end cap 106. As the proximal portion of the sleeve 102 is advanced towards the end cap 106 and the distal portion of the sleeve 102 which is axially fixed to the cannula shaft 14 by the end cap 106, the distal portion of the sleeve 102 is moved to a deployed configuration in which the distal portion of the sleeve 102 bows or pivots outwardly to form an anchor member 172 (FIG. 4) to retain the distal portion of the cannula assembly 10 within the body cavity "BC".

In embodiments, the outer surface of the cannula shaft 14 includes annular ribs 80 (FIG. 2) that project outwardly from the longitudinal axis "X" of the sleeve 102 (FIG. 2) into contact with the inner surface of the sleeve 102. Contact between the annular ribs 80 and the inner surface of the sleeve 102 helps to maintain the axial position of the sleeve 102 in relation to the catheter shaft 14. The sleeve 102 includes the deformable mesh material and a thin rigid plastic cover 103 that extends from the upper end of the sleeve 102 mesh material to a lower portion of the sleeve mesh material, leaving the deployable anchor member 172 uncovered by the cover 103 (see FIG. 2).

Figure 4:
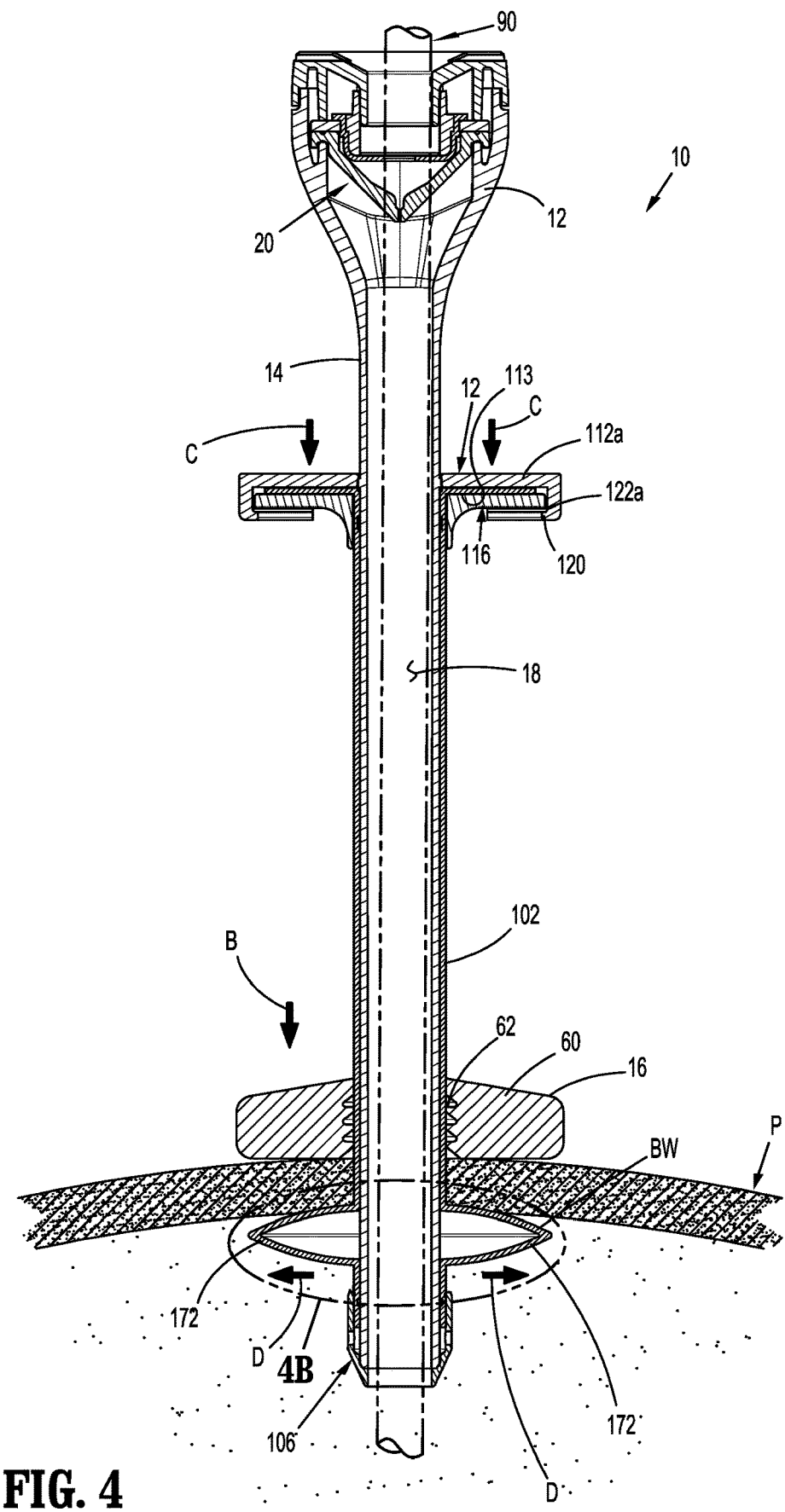
FIG. 4 is a cross-sectional view taken along section line 4-4 of FIG. 1 with the anchor member in a deployed configuration.
Figure 6:
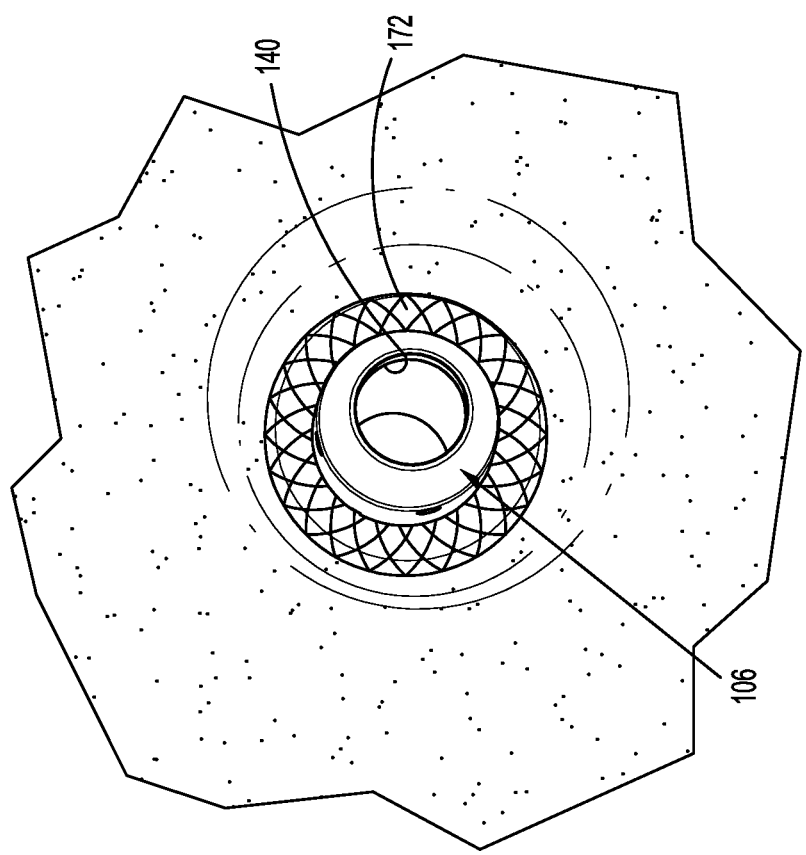
FIG. 6 is a perspective view from within the body cavity of the distal portion of the cannula assembly of FIG. 4A as the anchor member deactivates in response to an excessive force applied to the cannula assembly.

In certain embodiments, the distal portion of the sleeve 102 can include a notch 170 (FIG. 3) to facilitate movement of the distal portion of the sleeve 102 to the deployed configuration (FIG. 4). The notch 170 can define a weakened portion of the sleeve 102 that is provided to better control the location of the deployment of the anchor member 172 as the proximal portion of the sleeve 102 is advanced towards the end cap 106. More specifically, the notch 170 can define a hinge or pivot location for the anchor member 172. In other embodiments, the notch is omitted.

In embodiments, the sleeve 102 is formed from a biocompatible mesh material such as polyethylene terephalate or PET or other medical grade thermoplastic, that has strength characteristics to allow the anchor member 172 of the sleeve 102 to deactivate or move towards a reduced diameter configuration when the cannula assembly 10 is in the deployed configuration and the cannula assembly 10 is pulled with a force that is capable of tearing tissue. More specifically, the mesh material should be selected to provide an anchor member 172 that will fold downwardly towards a side wall of the cannula shaft 14 to allow the distal portion of the cannula assembly 10 to be removed from an incision "I" in the patient "P" when an excessive force is applied to the cannula assembly 10. Characteristics of the mesh material to consider when selecting the appropriate material include mesh filament modulus of elasticity and tensile strength, mesh filament diameter, inside and outside diameters of the anchor member 172, and environmental parameters, e.g., temperature of the body cavity. The inside and outside diameters of the anchor members 172 will depend in large part of the diameter of the cannula shaft 14. It is also noted that the mesh material should be sufficiently rigid to translate movement of the grip assembly 104 to movement of a distal portion of the sleeve 102.

In some embodiments, a mesh cover 176 is attached to the outer surface of the mesh. The mesh cover 176, which may be a semi-transparent film, prevents the mesh from rubbing against and irritating tissue, but allows the anchor to expand. The mesh cover material and geometry should also be considered when selecting the appropriate mesh material to form the sleeve 102.

Referring to FIG. 3, when the cannula assembly 10 is used during a surgical procedure, the distal portion of the cannula assembly 10 including the end cap 106, the distal portion of the cannula shaft 14, and the distal portion of the sleeve 102 are inserted through an incision "I" in the direction indicated by arrow "A" into the body cavity "BC". The cannula assembly 10 is inserted into the body cavity "BC" with the sleeve 102 in a non-deployed configuration and the grip assembly 104 in its proximal or retracted position.

Referring to FIG. 4, in order to fix or anchor the cannula assembly 10 within the body cavity "BC" and secure the cannula assembly 10 to a body wall "BW" of the patient "P", the outer fixation device 16 is slid in the direction indicated by arrow "B" about the cannula shaft 14 and the sleeve 102 into contact with the patient "P". The grip assembly 104 is also moved about the cannula shaft 14 in the direction indicated by arrows "C" to move the sleeve 102 about the cannula shaft 14 towards the end cap 106. As discussed above, movement of the grip assembly 104 about the cannula shaft 14 moves the proximal portion of the sleeve 102 towards the distal portion of the sleeve 102, which is axially fixed to the distal portion of the cannula shaft 14 by the end cap 106, to bow or move the distal portion of the sleeve 102 outwardly in the direction indicated by arrows "D" to deploy the anchor member 172. At this time, surgical instruments 90 can be inserted through the seal assembly 20 and through the channel 18 of the cannula shaft 14 to perform the surgical procedure. Deployment of the anchor member 172 also functions to provide a seal between the outer surface of the cannula shaft 14 and sleeve 102 and the walls defining the incision "I". The mesh cover 176 can be blow molded to form the shape of the anchor, which is formed in a shape that improves the seal with the patient's body. The deployed anchor member 172 has an upper side 172a that engages the inner tissue around the incision, and preferably forms a sloping or curved shape. (See FIG. 4B).

Figure 5:
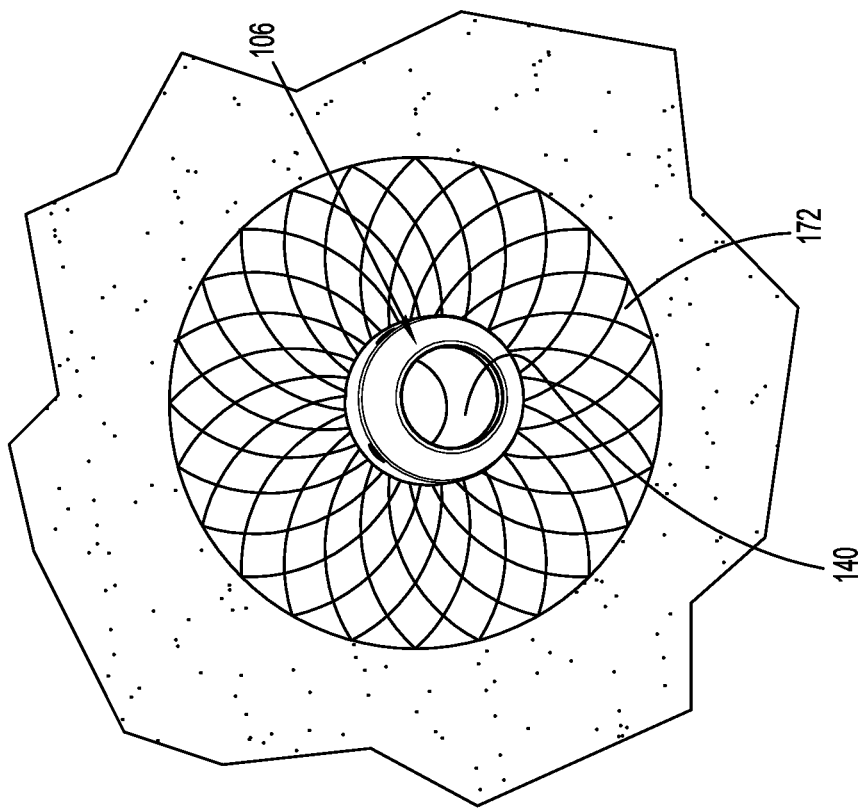
FIG. 5 is a perspective view from within a body cavity of a distal portion the cannula assembly of FIG. 4 with the anchor member in the deployed configuration.

Referring to FIGS. 4A-6, if a force is applied to the cannula assembly 10 in the direction indicated by arrow "E" with the anchor member 172 deployed as shown in FIGS. 4 and 5, the sleeve 102 is formed of a material that will allow the anchor member 172 to deactivate or fold inwardly (or deactivate) in the direction indicated by arrow "F" towards the longitudinal axis "X" of the sleeve 102 to allow the distal portion of the cannula assembly 10 to exit the incision "I" before the tissue defining the incision "I" begins to tear. As such, the anchor member 72 of the inner fixation device 100 will automatically deactivate when an excessive force is applied to the cannula assembly 10 to prevent tearing or ripping of tissue.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A cannula assembly comprising:
a housing defining a receptacle;
a seal assembly positioned within the receptacle, the seal assembly being adapted to form a seal about a surgical instrument inserted through the housing;
a cannula shaft extending from the housing and defining a channel, the channel defining a longitudinal axis and having a proximal portion that communicates with the receptacle and an open distal end; and
a sleeve having a proximal portion movably positioned about the cannula shaft and a distal portion axially fixed to a distal portion of the cannula shaft, the sleeve including a deformable mesh material having a deployable anchor member and a thin cover that extends from the proximal portion of the sleeve to a lower portion of the sleeve, leaving the deployable anchor member unrestrained by the cover;
a frustoconical end cap attached to the cannula shaft at the distal end thereof so as to cover the distal portion of the sleeve, the end cap including one or more holes for receiving an adhesive material;
wherein movement of the proximal portion of the sleeve towards the distal portion of the sleeve causes the anchor member of the sleeve to move radially outward away from the longitudinal axis of the cannula shaft, the anchor member being formed of a material that is configured collapse against the cannula shaft when a force is applied to the cannula assembly to facilitate removal of the cannula assembly from within a body cavity of a patient.

2. The cannula assembly of claim 1, wherein the cover is formed of a transparent material.

3. The cannula assembly of claim 1, further including a grip assembly secured to the proximal portion of the sleeve.

4. The cannula assembly of claim 3, wherein the sleeve includes a flange that extends radially outwardly.

5. The cannula assembly of claim 4, wherein the grip assembly includes a first portion and a second portion, the flange being clamped between the first and second portions of the grip assembly.

6. The cannula assembly of claim 1, further including an outer fixation member slidably positioned about the cannula shaft.

7. The cannula assembly of claim 6, wherein the outer fixation member is positioned about the sleeve and the cannula shaft.

8. The cannula assembly of claim 7, wherein the housing includes a fluid port that defines a bore that communicates with the receptacle.

9. The cannula assembly of claim 7, wherein the housing of the cannula assembly supports a valve housing that is positioned to control fluid flow through the bore of the fluid port.

10. The cannula assembly of claim 9, wherein the valve is a rotary valve.

11. A cannula assembly comprising:
a housing defining a receptacle;
a seal assembly positioned within the receptacle, the seal assembly that is adapted to form a seal about a surgical instrument inserted through the housing;

a cannula shaft extending from the housing and defining a channel, the channel defining a longitudinal axis and having a proximal portion that communicates with the receptacle and an open distal end; and a sleeve having a proximal portion movably positioned about the cannula shaft and a distal portion axially fixed to a distal portion of the cannula shaft, the sleeve being formed from a mesh material, the mesh material including mesh filaments, the sleeve including a protective cover;

wherein movement of the proximal portion of the sleeve towards the distal portion of the sleeve causes the distal portion of the sleeve to move outwardly from the longitudinal axis of the cannula shaft to form an anchor member adjacent the distal portion of the cannula shaft, the protective cover extending from the proximal portion of the sleeve and leaving the anchor member uncovered.

12. The cannula assembly of claim 11, further including a grip assembly secured to the proximal portion of the sleeve.

13. The cannula assembly of claim 12, wherein the grip assembly includes a first portion and a second portion and the sleeve defines a flange, the flange of the sleeve being clamped between the first and second portions of the grip assembly.

14. The cannula assembly of claim 11, further including an end cap supported on the distal portion of the cannula shaft, wherein the distal portion of the sleeve is axially fixed in relation to the cannula shaft between an inner surface of the end cap and an outer surface of the cannula shaft.

15. The cannula assembly of claim 14, wherein the end cap defines one or more holes for receiving an adhesive material.

* * * * *